United States Patent [19]
Christoudias

[11] Patent Number: 5,234,444
[45] Date of Patent: Aug. 10, 1993

[54] CHRISTOUDIAS KNOT—TRANSFER METHOD AND INSTRUMENT

[75] Inventor: George C. Christoudias, New Milford, N.J.

[73] Assignee: Cyprus Endosurgical Tools, Inc., Saddle River, N.J.

[21] Appl. No.: 804,897

[22] Filed: Dec. 6, 1991

[51] Int. Cl.[5] ............................................. A61B 17/00
[52] U.S. Cl. ........................................ 606/148; 606/1; 606/139; 128/898
[58] Field of Search .................... 606/148, 139, 144

[56] References Cited

U.S. PATENT DOCUMENTS 3,871,379  3/1975  Clarke ................................. 606/148
5,084,058  1/1992  Li ........................................ 606/148

Primary Examiner—Stephen C. Pellegrino
Assistant Examiner—Jeffrey A. Schmidt
Attorney, Agent, or Firm—Richard A. Joel

[57] ABSTRACT

The invention comprises an elongated cylindrical instrument and a method for extracorporeal knot tying in endoscopic surgery. The Christoudias knot-transfer instrument includes a solid stem of substantially cylindrical cross section with two diametrically opposite longitudinal grooves along its outer surface. These grooves converge at an angle of 100 degrees towards the axis of the cylinder at the head of the instrument, and at an angle of 150 degrees towards the axis of the cylinder at the tail of the instrument. In accordance with the method herein, this instrument pushes a knot which is tied extracorporeally with its head, through a port and into the tissues to be ligated or on top of another knot. The ends of the surgical thread slide along the grooves. Many knots can be tied and delivered to said tissues in an extremely expeditious manner.

5 Claims, 5 Drawing Sheets

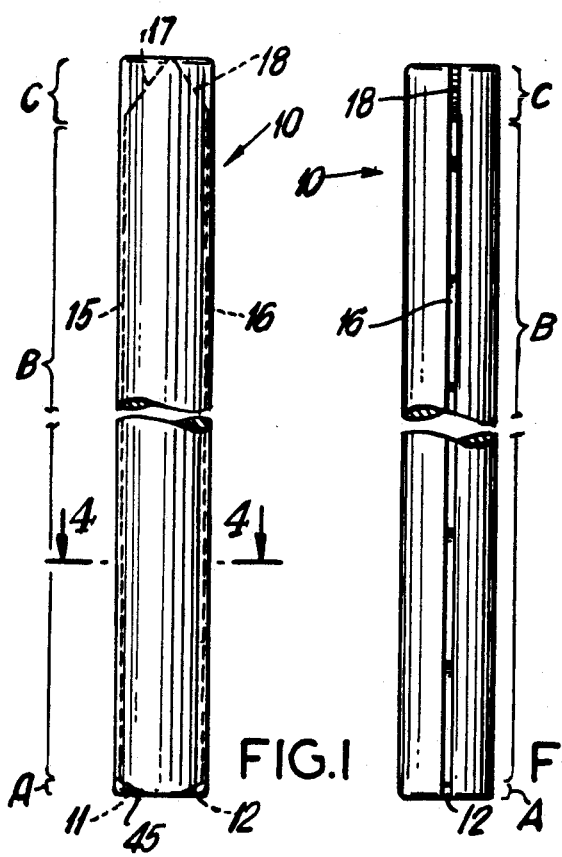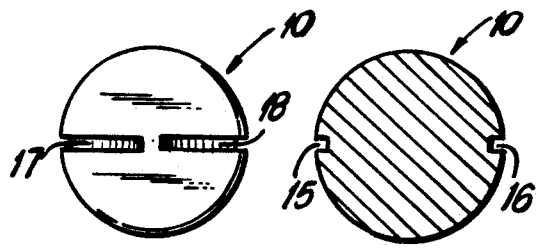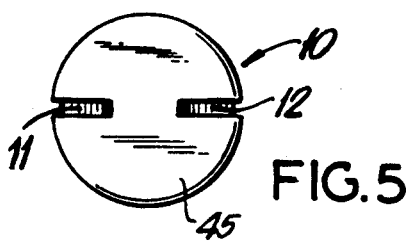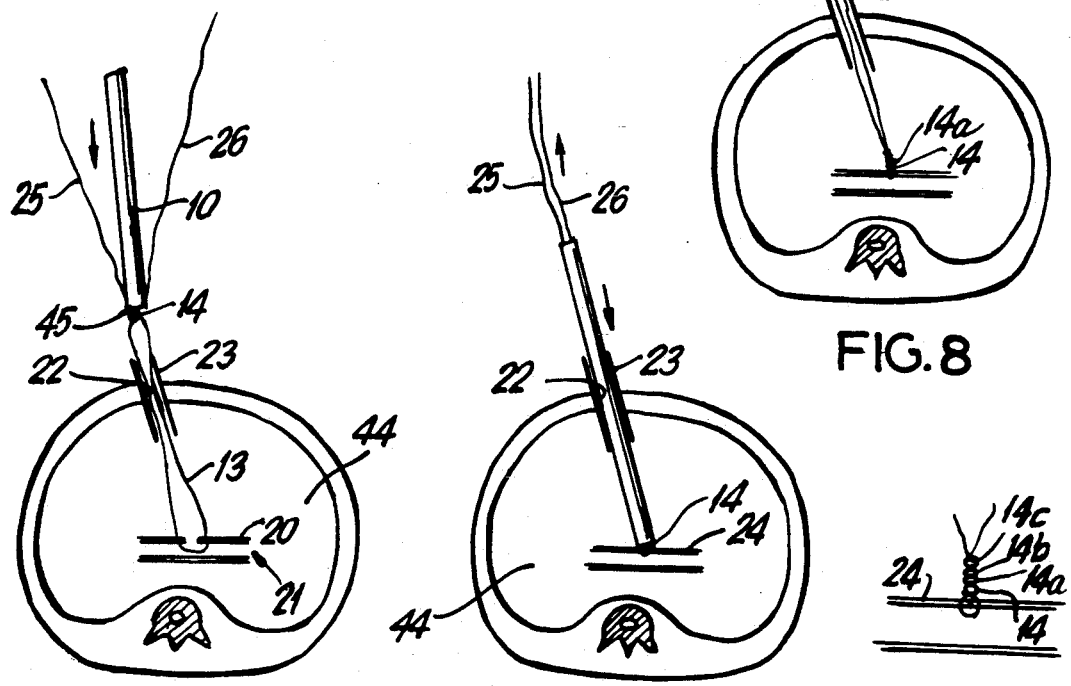

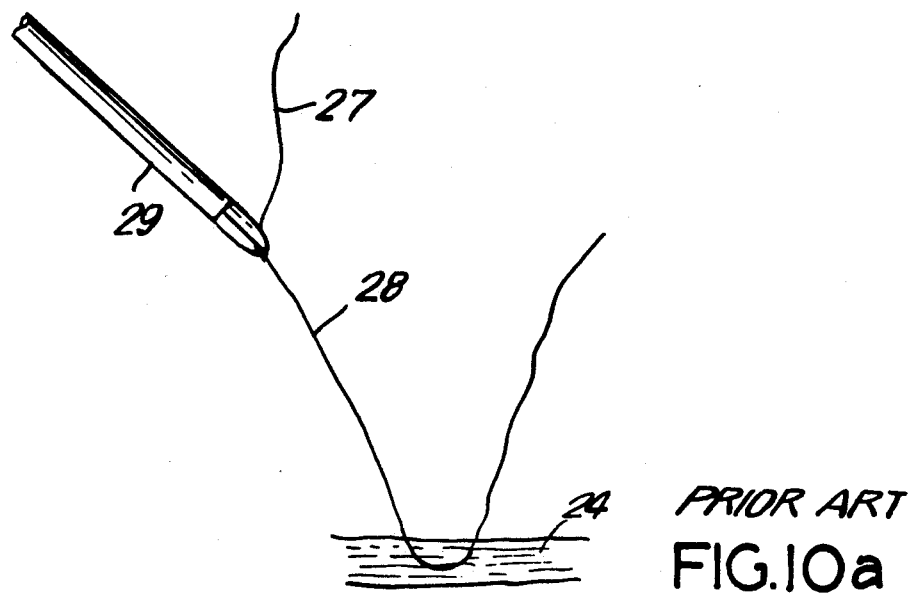
PRIOR ART
FIG. 10a
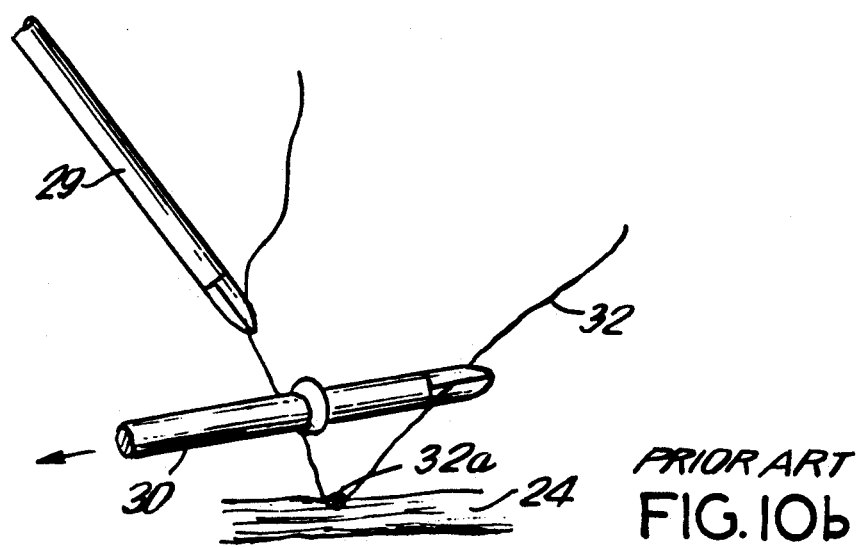
PRIOR ART
FIG. 10b
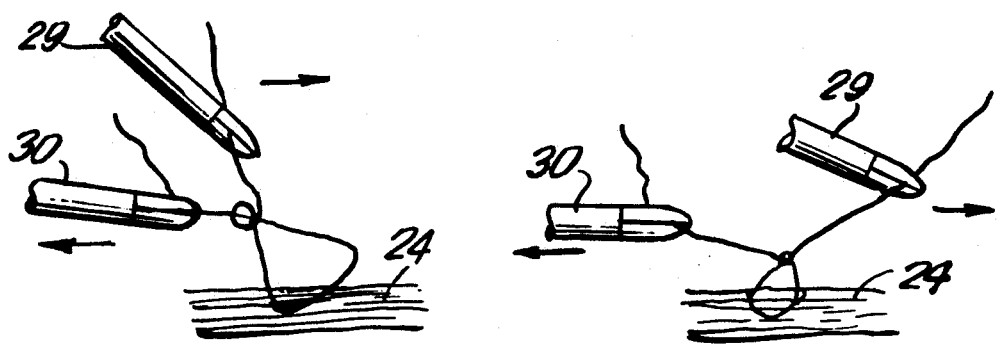
PRIOR ART
FIG. 10c
PRIOR ART
FIG. 10d

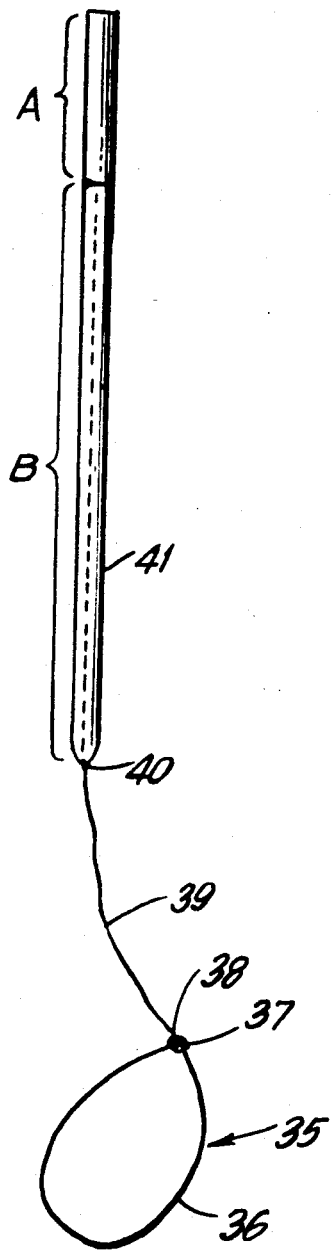
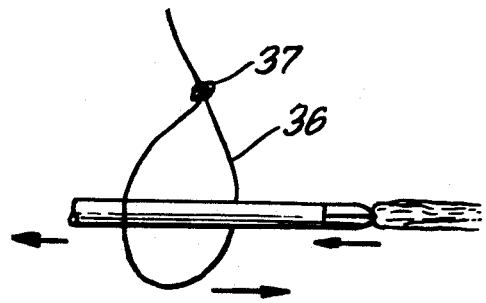
PRIOR ART
FIG. 11c
PRIOR ART
FIG. 11d
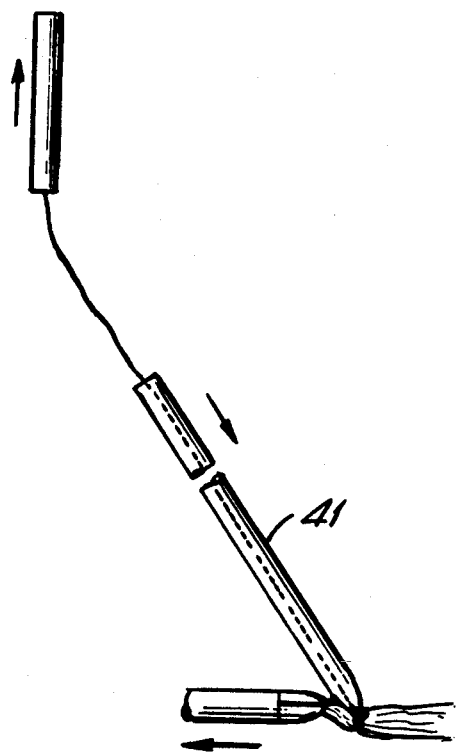
PRIOR ART
FIG. 11a
PRIOR ART
FIG. 11b

CHRISTOUDIAS KNOT—TRANSFER METHOD AND INSTRUMENT

BACKGROUND OF THE INVENTION

The knot transfer instrument of the present invention is designed to deliver more than one extracorporeally tied knot, one at a time, into the body cavity in laparoscopic surgery achieving effective ligation of tissues or vessels in a similar manner to that achieved in conventional surgery.

With more and more procedures being performed with the laparoscopic method, there is a great need for an instrument that will allow the surgeon to tie multiple knots in securing ligation or approximation of tissues inside a body cavity in a manner similar to that achieved in conventional surgery. There is no prior art that allows the application of multiple knots with extracorporeal knot tying in endoscopic surgery. At the present time, there are two methods of tying knots in endoscopic surgery: a) Intracorporeal knot tying and b) Extracoporeal knot tying.

a) Intracorporeal knot tying. This method involves instrument tying and is accomplished by holding the one side (limb) of the thread with one instrument, looping said thread over a second instrument, which second instrument then grasps the other side (limb) of the thread and by a withdrawing motion passes it through the loop and accomplishes the formation of a knot which is then brought down to the tissues to be ligated or approximated. By repeating the steps, multiple knots can be thrown as in conventional surgery. This method of intracorporeal knot tying is very cumbersome, time consuming and is inadequate for the surgeons currently performing endoscopic surgery.

b) Extracorporeal knot tying. Currently, there is a method of extracorporeal knot tying which involves the throw of a single compound knot (Roeder's Knot), which may or may not be preformed. The preformed knot is a part of a system commonly called endoloop and involves the formation of a loop by the creation of a single compound knot (Roeder's Knot) on the end of a thread. The other side of the thread passes through the center of a rigid rod and is firmly attached to the end portion of this rigid rod. The part of the rod through which the thread is passed can be broken off the part which is firmly attached to the thread. The way that this loop with the knot is used to ligate tissue is as follows. The loop with the rod is advanced into the abdominal cavity through a standard port. A grasper forceps is passed through the loop and is used to grasp the tissue to be ligated which it pulls through the loop. The intermediate part of the rigid rod is then broken off the top part of the rigid rod and advanced over the thread to the knot while the thread is pulled in the opposite direction with the top part of the rod. The intermediate part of the rod then positions the knot over the tissue to be ligated until the loop is closed thereover. The rod is then withdrawn from the abdominal cavity and the thread cut.

The non-preformed knot (Endosuture) is a system which is identical with the endoloop system except for the fact that there is a needle at the end of the thread and there is no knot or loop. The way that this system is used is as follows. The needle is advanced into the abdominal cavity with a needle holder and then passed through and/or around the tissue to be ligated and again withdrawn from the abdominal cavity. The needle is then cut off and a fisherman's knot is tied, thus forming a loop. Following the same steps as with the endoloop the knot is then advanced to the tissue to be ligated and the loop closed over said tissue to complete the operation.

The present invention represents an enormous advance in endoscopic surgery. Using the instrument and technique disclosed herein it is possible to rapidly tie knots extracorporeally and immediately transfer the knots internally to the tissue being ligated. A plurality of knots may be transfered intracorporeally expeditiously with the same ease as conventional surgery.

SUMMARY OF THE INVENTION

The knot transfer instrument of the present invention comprises an elonagated cylindrical rod with diametrically opposite smooth grooves along its outer surface running parallel to its axis and converging in a predetermined manner at both ends of the rod towards the axis of the instrument. Said grooves will accommodate the limbs of the surgical thread and will slide over the thread in an endoscopic operation while delivering repeated knots from outside a body cavity, through a port, intracorporeally, to the tissue to be ligated. This procedure could be accomplished with any suture presently on the market which has a thread of adequate length and a needle that could fit through a port in use. The method and instrument disclosed in this invention permit the rapid extracorporeal formation of knots and their transfer to ligated tissue within a body cavity through a body port.

Accordingly, a main object of this invention is to provide a method and instrument to apply multiple knots formed extracorporeally in the conventional method (hand tied) to tissue in a body cavity through a port in an endoscopic surgery procedure.

A second object of this invention is to provide a new and improved instrument that can be used repeatedly to apply knots with different sutures to tissue in endoscopic surgery and is not discarded after a single use which is the case with the endoloop and endosuture techniques.

A third object of this invention is to provide a new and improved instrument and method which can be used in endoscopic surgery in conjunction with sutures presently on the market, and currently used in conventional surgery which is not the case with the endoloop and endosuture procedures.

A more specific object of this invention is to provide a new and improved method and device for tying a plurality of knots in endoscopic surgery much faster and economically utilizing a unique knot transfer instrument to move the externally formed knot internally to the tissue being ligated.

DESCRIPTIONS OF THE DRAWINGS

The above and other objects and advantages of the current invention may be more clearly seen when viewed in conjunction with accompanying drawings wherein:

FIG. 1 is a front view of the invention with the grooves running along the side of the instrument surface and converging at both ends at a predetermined angle, FIG. 2 is a side view of the invention with the one groove extending along the entire length of the instrument and directed towards the axis at both ends of the instrument, FIG. 3 illustrates the extracorporeal end of the instrument, FIG. 4 is a cross section of the shaft of the instrument taken along the line 4—4 of FIG. 1, FIG. 5 is an end view of the intracorporeal end of the instrument which transfers a knot within a body cavity, FIG. 6 illustrates the instrument applied on a formed knot to be delivered to the tissues with FIGS. 6-8 illustrating the knot tying method of the invention;

FIG. 7 shows the instument upon completion of the knot delivery to the tissues inside the abdominal cavity, FIG. 8 shows the completion of delivery of 4 knots to the tissue being ligated, FIG. 9 shows the completed knot application with the threads cut and the function of the invention fulfilled, FIGS. 10a-d illustrate a prior art intracorporeal knot tying technique used in endoscopic surgery, FIGS. 11a-d illustrate a prior art extracorporeal knot tying technique used in endoscopic surgery known as the endoloop technique, FIGS. 12a-d illustrate a prior art extracorporeal knot tying technique used in endoscopic surgery known as the endosuture technique, and FIGS. 13a-c illustrate an alternate embodiment of the invention including a knot-trapping platform.

DETAILED DESCRIPTION OF THE INVENTION

Figure 12A:
Figure 12C:
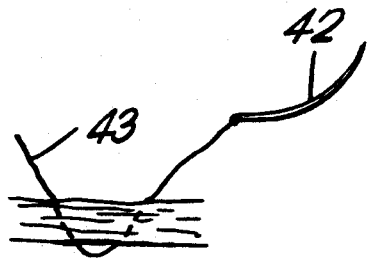
Figure 12B:
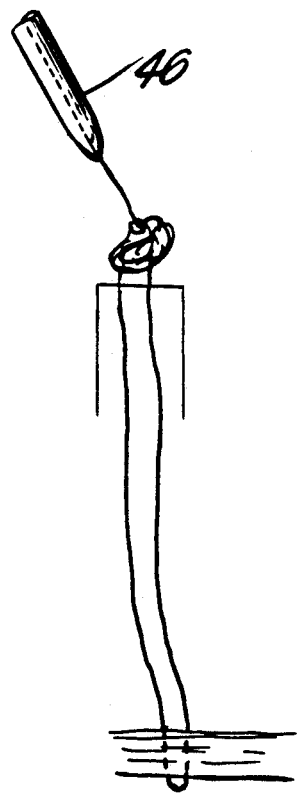
Figure 12D:

Refering now to FIGS. 1 and 2, the invention comprises a rigid cylindrical rod 10 of surgical steel or plastic which is divided into 3 parts. Part A which includes the begining of the 2 driver grooves 11 and 12 diametrically opposite each of them starting 1.25 mm from the axis of the instrument and extending towards the periphery of the shaft B at an angle of 80 degrees with the main axis of the instrument (FIG. 1). Said grooves 11 and 12 will accomodate the thread limbs 25, 26 distal to the knot 14 to be delivered in the abdominal cavity 44.

Part B or shaft 10 of the instrument extends from the point where the continuing grooves 11 and 12 of part A meet the periphery of the instument and extends to the point where the grooves 15,16 are directed towards the axis of the instrument where part C begins. Part B, the shaft 10, of the instrument is a solid, cylindrical structure with two grooves 15,16 parallel to the main axis extending along its surface at diametrically opposite sides. Said grooves 15,16 will accommodate the thread limbs 13 and allow said thread limbs to slide inside the continuing grooves 11,12 and 14,15 while the knot formed by the thread limbs 25,26 is delivered into the abdominal cavity 44 and onto the tissues.

Part C starts at the point where the grooves 15,16, described above converge as grooves 17,18 to the center of the cross section of the instrument at its main axis at an angle of 150 degrees with the grooves 15,16 of the shaft 10.

The convergence of the grooves 17,18 secure firmly the thread limbs 13 which are held further away with the fingers while the instrument slides along said thread limbs 25,26 and delivers the formed knot 14 in engagement with driver face 45 to its destination. The length of the instrument (A+B+C) is about 30 cm and is easily manipulated.

Referring now to FIG. 6, a suture is placed through the edges 22 and 20 of the bowel 21 to be approximated and both the limbs 25, 26 of the suture thread 13 are presented outside the abdominal cavity 44 through a regular port 23. A knot 14 is formed in the conventional manner outside the body cavity 44 and the Christoudias knot transfer rod 10 placed on the knot 14. The limbs 25, 26 of the thread 13 then placed into the grooves 11, 12, 15, 16 and 17, 18 of the instrument 13 thus engaging the knot 14 onto the intracorporeal driver end 45 of the instrument and within the space between the begining of the grooves (FIG. 4). The two limbs 25, 26 of the thread 13 are then held firmly with the one hand while the other hand advances the knot transfer rod 10 through the port 23 and into the abdominal cavity 44 (FIG. 7) while sliding the knot 14 down to the desired from the abdominal cavity 44, disengaged from the limbs 25,26 of the thread 13 and a new knot 14a is formed in the conventional method. Said knot 14a is delivered in the same manner into the abdominal cavity 22 and onto the first knot 14. A third knot 14b and fourth 14c, etc. can be formed and delivered onto the previous knot thus accomplishing extracorporeal multiple knot tying, see FIGS. 6-8.

The prior art, as discussed previously, includes intracorporeal knot tying as shown in FIGS. 10a-d. This method involves instrument tying and is accomplished by holding one limb (side) 27 of the thread 28 with one instrument 29 and looping the thread 28 over a second instrument 30. The other side or limb 32 is grasped by the second instrument 30 and by a withdrawing motion passes it through the loop causing the formation of a knot 32 which is moved down to the tissues 24. The method is very time consuming and cumbersome.

Another prior art technique, shown in FIGS. 11a-11d, is extracorporeal knot tying which involves the single compound knot or endoloop 35 which may or may not be preformed. A single loop 36 is formed by a single compound knot 35 on one end of the thread 39. The other end of the thread 39 passes through a central aperture 40 in instrument 41 and is firmly attached at the other end of 41. Part B of the instrument 41 through which the thread extends can be broken off at Part A which is firmly attached to the thread 39. The method of endoloop suturing with the foregoing was previously described in connection with the Background of the Invention.

The prior art endosuture technique shown in FIGS. 12a-12d, is similar to the endoloop system except for the fact that there is a needle 42 at the end of the thread 43 and there is no knot or loop. In use, the needle 42 is advanced into the abdominal cavity 44 with a needle holder and then passed through and/or around the tissue to be ligated and then withdrawn. The needle 42 is cut off and a fisherman's knot formed.

In an alternate embodiment of the invention the cylindrical rod 10 includes driver grooves 11, 12 and grooves 14, 15 extending axially along the surface substantially in the same plane. The thread limbs 25, 26 would slide within said grooves 11, 12 and 14, 15 in a knot transfering operation with the ends of the long thread being held by the surgeon and the instrument 10 transferring the knot 14 to the tissue. If one limb (or end) 25 or 26 of the thread 13 is too short to advance outside the body cavity 44, an instrument approximately 3 mm in length can be used through the same port 23 to grasp the short end of the thread 13 thereby forming an extension of the thread to the outside. A knot 14 is then tied over the extension instrument and transfered into the body cavity 44 with driver face 45 beyond the tip of the extension instrument and over the short hand accomplishing the same purpose as if the thread extended extracporeally.

Figure 13A:
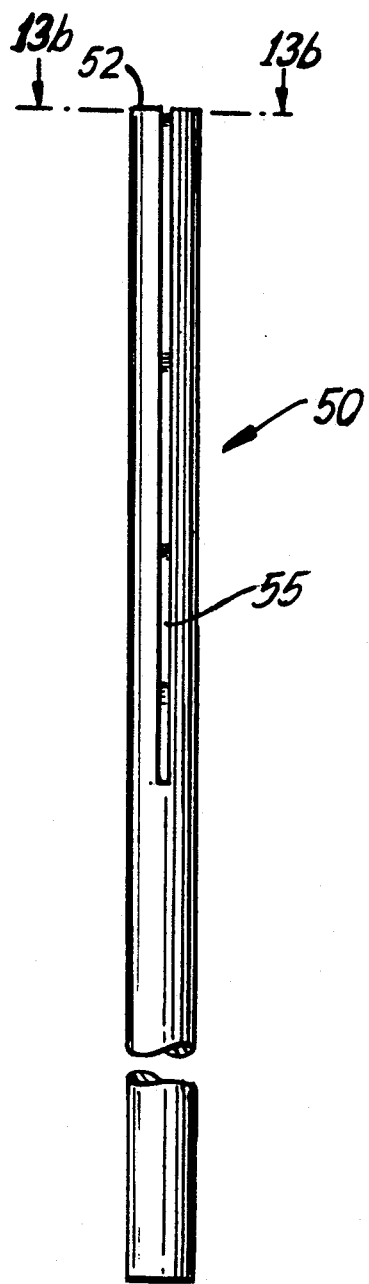
Figure 13B:
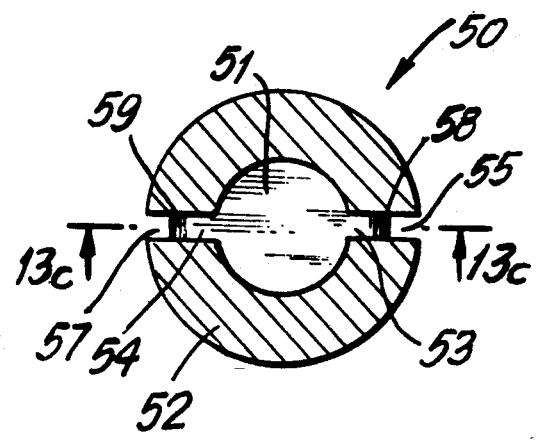
Figure 13C:
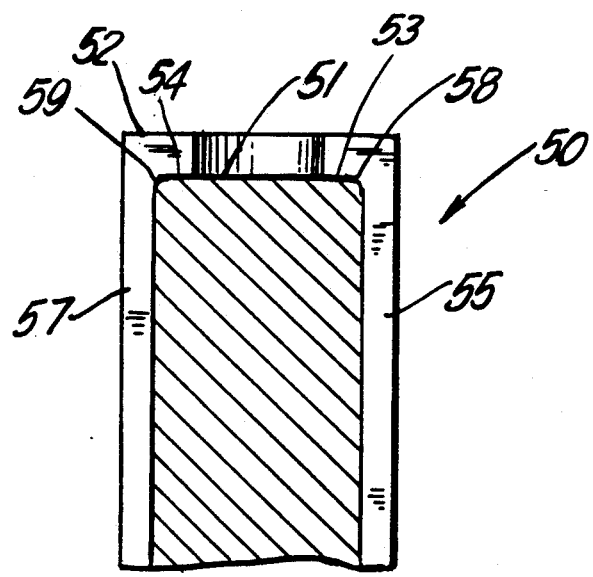

FIGS. 13a–c illustrate an alternate preferred embodiment of the invention which includes a circular central depression 51, 1.5 mm deep by 5 mm in diameter, on the driving end 52 of the instrument 50. The depression 51 traps the knot (not shown) and prevents it from slipping during transfer. Starting at diametrically opposite sides of the depression 51 are two radial grooves 53, 54, 1.5 mm deep by 1 mm wide by 1 mm long which are then connected by an arc 58, 54 of 0.5 mm with grooves 55, 57, 1 mm deep extending along the periphery 56 of the instrument 50 parallel to the main axis for a distance of 100 cm, the length of the instrument 50 being 400 mm. This embodiment has the added advantage of preventing knot slippage while providing the advantages of the previously discussed designs.

As can be readily seen the present invention represents a totally new knot tying instrument and method which facilitates the tying of multiple knots in endoscopic surgery. The invention represents an important advance which will facilitate the growth of endoscopic surgical techniques.

While the invention has been explained by a detailed description of certain specific embodiments, it is understood that various modifications and substitutions can be made in any of them within the scope of the appended claims which are intended also to include equivalents of such embodiments.

What is claimed is:

1. A knot transfer instrument for knots formed from the limbs of thread used to ligate tissue through a body cavity port in endoscopic surgery comprises:
    an elongated rod having, an upper end and a distal end, a diameter fitting within the body cavity port, an outer surface, and a pair of diametrically opposite grooves extending axially along the outer surface of said rod, said grooves each converging towards the axis at the distal end but remaining separate, and a driver face formed on said digital end to engage a knot,
    wherein the rod is substantially cylindrical and includes a transverse face at each end, providing a predetermined separation between the grooves on the face to engage the knot and said grooves converge inwardly towards the axis of the rod at the upper end beginning at a greater axial distance from the upper end than from the distal end, and
    wherein a knot in a thread coupled to tissues within a body cavity is formed outside the body cavity port and wherein the limbs of said thread extend outwardly from the knot along the grooves in the instrument and slide therealong into the body cavity by movement of said instrument.

2. A knot transfer instrument in accordance with claim 2 wherein:
    the grooves converge inwardly towards the axis at an angle in the area of 100 degrees at the distal end and at an angle in the area of 150 degrees at the upper end, said angles being measured from a plane perpendicular to the axes of the rod.

3. A knot transfer instrument in accordance with claim 1 wherein:
    the rod is approximately 5 millimeters in diameter and the grooves are 0.5 millimeters deep along the surface of the rod prior to convergence at the distal and upper ends.

4. A knot transfer instrument in accordance with claim 1 wherein:
    the rod is substantially cylindrical and approximately 30 cm in length.

5. The method of transferring a knot in a thread used to ligate tissues within a body cavity in endoscopic surgery comprising the steps of:
    inserting a thread through adjacent ends of tissue within a body cavity and having the ends of the thread extending outwardly from said cavity,
    hand-forming a knot in the thread outside the body cavity,
    providing an elongated instrument having diametrically opposed grooves extending axially therealong on the surface and an upper face and a lower driver face,
    engaging the ends of the thread within and along the grooves in the instrument,
    engaging the knot with the driver face,
    transferring the knot into the body cavity by inserting the instrument through a port into the body cavity while the thread slides along the grooves in the instrument, and
    wherein the instrument includes a flat driver face for engaging the knot and wherein the grooves converge towards the axis adjacent the upper face and lower driver face of the instrument to facilitate sliding of the thread therealong.

* * * * *